United States Patent [19]
Schaar

[11] 3,935,768
[45] Feb. 3, 1976

[54] METHOD OF MAKING A DISPOSABLE DIAPER

[75] Inventor: Charles H. Schaar, Lake Zurich, Ill.

[73] Assignee: Colgate-Palmolive Company, New York, N.Y.

[22] Filed: June 6, 1974

[21] Appl. No.: 476,952

Related U.S. Application Data

[62] Division of Ser. No. 296,982, Oct. 12, 1972, Pat. No. 3,837,955, which is a division of Ser. No. 111,188, Feb. 1, 1971, Pat. No. 3,731,689.

[52] U.S. Cl. ............................. 83/39; 83/47; 83/54; 83/176; 83/408
[51] Int. Cl.² ............................................. B26D 3/00
[58] Field of Search .............. 83/17, 18, 39, 46, 47, 83/54, 176, 408; 93/8 VB, 14, 17, 18, 19, 21, 25, 26, 33 R, 35 SB, 35 VL; 156/510; 225/38

[56] References Cited
UNITED STATES PATENTS

| | | | |
|---|---|---|---|
| 1,770,056 | 7/1930 | Woods | 83/176 |
| 2,209,209 | 7/1940 | Ruby | 83/39 X |
| 2,651,364 | 9/1953 | Ashman | 83/54 X |
| 3,229,875 | 1/1966 | Stoller | 225/38 |
| 3,726,745 | 4/1973 | Gidge et al. | 156/510 |
| 3,820,425 | 6/1974 | Cunningham | 83/54 X |

FOREIGN PATENTS OR APPLICATIONS

121,598  11/1970  Norway .................................. 83/46

*Primary Examiner*—J. M. Meister
*Assistant Examiner*—Fred A. Silverberg
*Attorney, Agent, or Firm*—Ellen P. Trevors

[57] ABSTRACT

An improved self-containable disposable diaper wherein a portion of the disposal pouch is slit so as to form integral, oppositely extending wings, the wings preferably having means thereon for completing the attachment of the diaper to an infant. A method is provided for forming the improved diaper featuring folding, slitting and refolding the portion thereof which is to define the pouch and wings.

4 Claims, 7 Drawing Figures

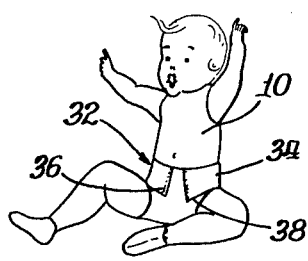
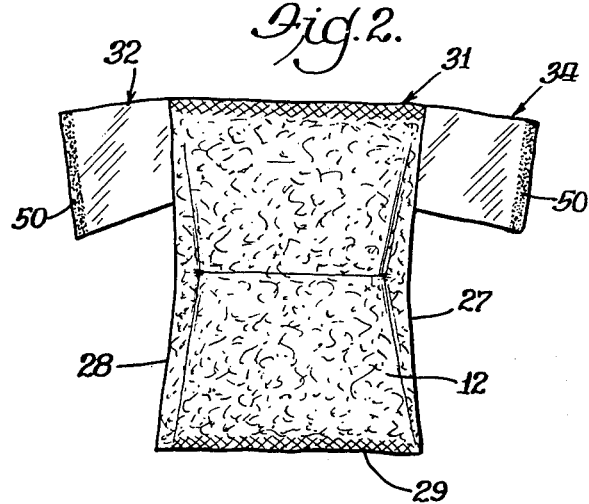
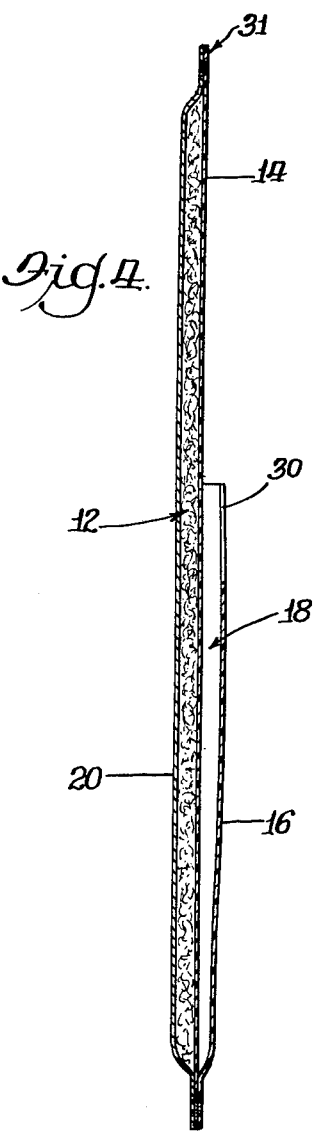
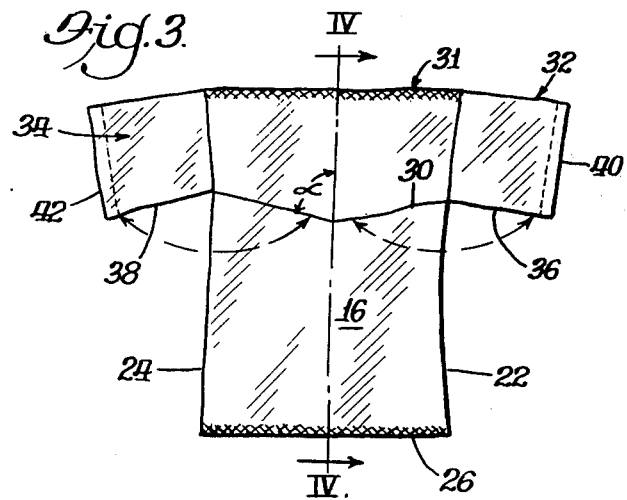
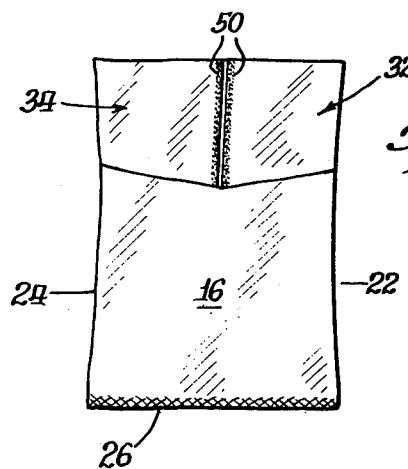

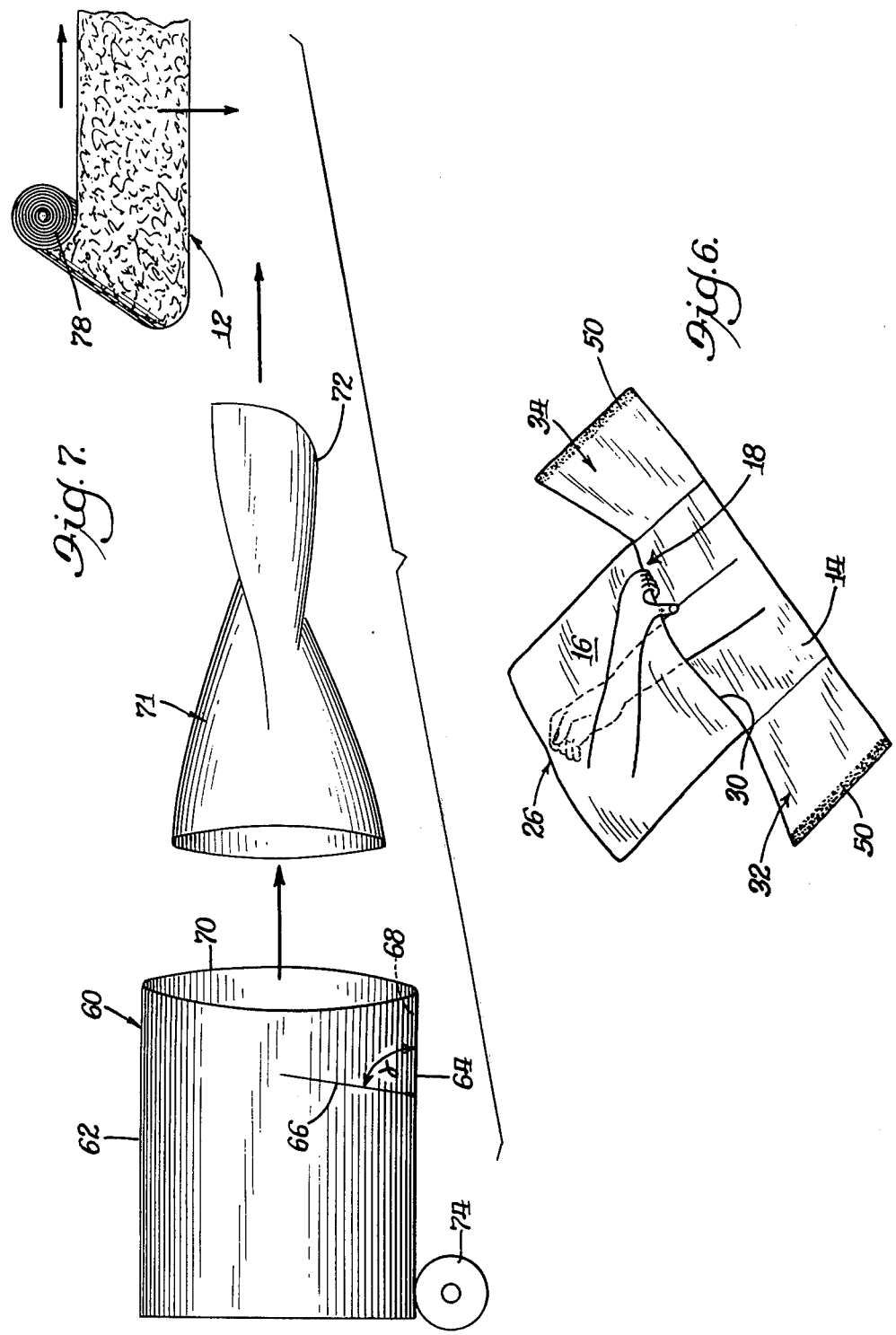

METHOD OF MAKING A DISPOSABLE DIAPER

This is a division of application Ser. No. 296,982 filed Oct. 12, 1972, now U.S. Pat. No. 3,837,955, which in turn is a division of application Ser. No. 111,188 filed Feb. 1, 1971, now U.S. Pat. No. 3,731,689 issued May 8, 1973.

This invention relates to a disposable diaper having an integral pouch and integral means for application to a baby, and to a method therefor.

U.S. Pat. No. 3,369,545 describes a disposable diaper and method of use which permits a soiled diaper to be contained within an integral pouch for sanitary disposal. While such a structure is highly advantageous, particularly in situations where immediate disposal of the soiled diaper is not feasible, it would be desirable if the diaper could be provided with integral means for fastening the diaper without the necessity for pinning it to itself through the pouch.

Various pinless diapers have been previously described in the literature. Thus, U.S. Pat. Nos. 2,627,858 and 3,089,494 describe diapers having extensions provided with adhesive for fastening without the need for safety pins. Although such structures are functional, they require the use of additional material in providing the pinless function.

In accordance with this invention, a disposable diaper of the type disclosed in the aforesaid U.S. Pat. No. 3,369,545 is provided with integral attachment means without the use of additional material. It will be apparent that the addition of function and structure without the use of additional material is economically attractive.

More specifically, the aforesaid diaper is improved by providing slits in the outermost wall of the pouch so as to define a pair of wings preferably having a combined width substantially equal to the width of the wall, and operable to form wings integrally extending from said wall in one of the waist regions of the diaper. According to the method of this invention, the pouch portion of the diaper is preferably made by flattening a tubular sheet of fluid impervious material to provide the two pouch walls and slitting through two opposing wall portions thereof along a line transverse to the longitudinal axis of the tube from a longitudinal edge of the flattened tube partially across the width of said flattened tube, and cutting a second slit along a line extending longitudinally from one end of the flattened tube to said transverse slit.

The structure of this diaper and the method therefor, will be better understood by reference to the following description of the invention and the accompanying drawings in which:

FIG. 1 is a perspective view of a baby wearing a diaper constructed in accordance with the invention;

FIG. 2 is a front elevational view of the absorbent side of the diaper constructed in accordance with the invention;

FIG. 3 is a rear elevational view similar to FIG. 2 except that the wings are folded outwardly so as to extend away from the diaper;

FIG. 4 is a sectional view taken along the line IV—IV of FIG. 3;

FIG. 5 is a rear elevational view of the diaper of FIG. 2 with the wings folded inwardly;

FIG. 6 is a fragmentary perspective view illustrating steps in the disposal of the diaper of the invention; and FIG. 7 is a schematic perspective view illustrating several of the improved steps in the method of making the diaper in accordance with the invention.

Referring to FIG. 1, the invention relates to a disposable diaper especially adapted for wear by a baby 10, the diaper being the type which is thrown away after having been soiled. Referring now to FIGS. 2-5, the invention particularly concerns the disposable diaper of the type having a fluid absorbent pad 12 and at least two layers 14 and 16 of fluid impervious sheet material attached to the pad 12 in such a manner as to form a pouch 18 (FIG. 4). The pad 12 preferably includes a fluid pervious cover sheet 20 as illustrated in FIG. 4. The layers 14 and 16 are connected at their edges 22, 24 and 26, these edges also coinciding with three of the edges 27, 28 and 29 respectively, of the pad 12 to define three of the edges of the diaper.

Various modifications are possible in the construction of the diaper of this invention, as illustrated in FIGS. 8 and 9 of the aforementioned U.S. Pat. No. 3,369,545. For example, the longitudinal edges of the cover sheet may be folded around the corresponding edges of the fluid absorbent pad, in which case the width of the back sheet need not be greater than the width of the fluid absorbent body. In this construction, the longitudinal edges of the back sheet are joined to the folded around longitudinal edges of the cover sheet.

Alternately the cover sheet may be larger than the absorbent pad. In this embodiment, the edges of the back sheet are secured to the folded around edges of the cover sheet. The diaper may also be constructed with both cover and back sheets having larger dimensions than the filler, and secured together in any of the aforementioned manners. In any of these embodiments, the pouch is formed by joining the impervious sheet at its longitudinal edges and one of its edges along the width thereof to the corresponding adjacent edges of the back sheet, as previously described.

Fluid impervious sheets 14 and 16 are preferably films of thermoplastic materials, thereby allowing construction of the diaper by heat sealing techniques. Examples of suitable thermoplastic films are polyethylene films, polypropylene films, ethylene-acrylate copolymer films, vinyl chloride polymer and copolymer films, etc.

Fluid absorbent pad 12 may be one or more plies of cellulosic sheeting, e.g., paper or non-woven fabric or a mass of loosely associated fibers such as cotton fibers or comminuted wood pulp commonly known as "fluff".

Cover sheet 20 can be a wet strength tissue paper, polyurethane foam, or preferably a non-woven fabric of material such as cotton, rayon, polypropylene, nylon, etc.

In accordance with one aspect of the invention, the outermost layer 16 is slit near one end 31 of the diaper along a line forming an edge 30 (FIG. 3) at an angle to edges 22 and 24 and along a longitudinal center line, to form a pair of integral wings 32 and 34 extending from opposite edges 22 and 24 of the layers 14 and 16 and of the diaper. The wings 32 and 34 are foldably attached to the bottom layer 14 so that the diaper can be stored (FIG. 5) with the wings 32 and 34 overlapping bottom layer 14. Because the wings are formed by slitting the layer 16, it will be readily apparent that the edges 36 and 38 of the wings are contiguous with the slit edge 30 of the layer 16 when the wings are so overlapped. Also, the outermost edges 40 and 42 of the wings are contiguous with each other in that overlapped configuration, the combined width of the wings being that of the width of the layers 14 and 16 and therefore of the diaper.

When the diaper is to be placed on the baby, the wings fold outwardly along the edges 22 and 24 to give the configuration shown in FIGS. 2 and 3. Although the wings 32 and 34 are disclosed as having approximate equal length, such is not necessary. Equal length does provide, however, a more aesthetic appearance.

In order to provide a contour fit of the wings around the baby's legs when the diaper is attached as shown in FIG. 1, it is necessary that edges 36 and 38 extend from the layer edges 22 and 24 at an angle less than 90°. Accordingly, the value of the angle "alpha" (FIG. 3) should be less than 90° and preferably about 77°. It will be readily appreciated that because of the angle alpha differing from 90°, the slit edge 30 forming the top outside edge of the pouch 18 is angled. Since, as disclosed, the wings 32 and 34 have approximate equal width, the location of the angle in the slit edge 30 is approximately centered in the layer 16. Thus, the wings 32 and 34 increase in their width as they extend outwardly from the edges 22 and 24 to their outermost edges 40 and 42, respectively. The increased width provides the additional advantage of increasing the attaching strength of the wings. The wing structure thus provides stronger attachment than could be had if conventional tape tabs were applied simply to the absorbent pad 12 or the liquid impervious sheet 14. If desired, wings 32 and 34 could be further reinforced by any means suitable for reinforcing impervious sheeting, such as an additional layer of liquid impervious film, strand reinforcements, etc., or by folding each wing back upon itself to provide a double thickness.

The pinless function of this diaper is preferably accomplished by applying a pressure sensitive adhesive to the zones indicated by the numeral 50, FIGS. 2, 5 and 6. Any conventional pressure sensitive adhesive can be used, examples being natural rubber combined with modified wood rosins and adhesives of the type disclosed in U.S. Pat. No. 3,299,010. Removable facing strips may be applied to the adhesive zones 50, so that the wings do not stick until the diaper is ready for use. Alternately, double-face pressure sensitive adhesive tabs can be used. The adhesive may be applied to an area other than zone 50; for example, it may be placed in a thinner or thicker band or as discrete spots.

The above-described diaper can be manipulated for disposal in a manner similar to the diaper disclosed in the aforesaid U.S. Pat. No. 3,369,545. That is, referring to FIG. 6 herein, the slit edge 30 of the layer 16 defines the opening into the pouch 18 which permits the turning inside out of the diaper. When the diaper is soiled, one hand is then slipped into the pouch 18 to the edge 26 of the layer 16 where that edge is grasped. At the same time the other hand pulls on the slit edge 30 of the layer 16, the two hands crossing over so as to turn the pouch inside out. The resulting configuration places the inside layer 14 completely exposed on one side of the folded up diaper with the layer 16 on the other side, the absorbent pad 12 being thus completely enclosed.

While the impervious sheet forming the wings and pouch need not be co-extensive with back sheet 16, it must have edges contiguous with at least one of the edges along the width of the diaper in order that the wings be in the waist region thereof. Furthermore, the pouch 14 must be of adequate dimensions so as to contain the entire soiled diaper surface upon reversal.

In accordance with another aspect of the invention, FIG. 7 illustrates a preferred method of manufacturing this diaper. In accordance with this method, the two layers 14 and 16 of the impervious sheet are extruded as a single tubular sheet 60. The sheet 60 is flattened so as to form fold longitudinal edges 62 and 64. The next step is to slit the flattened sheet through two opposing wall portions transversely from fold edge 64 along the slit line 66 only partially across the sheet. Preferably slit 66 extends one-half the width of flattened sheet 60. The line 66 is inclined to the fold 64 at an angle preferably less than 90°, the angle "alpha" for example being on the order of about 77°. A second slit is then cut along the line indicated by numeral 68 which coincides with the fold edge 64 and intersects the slit 66 as well as the leading edge 70 of the tubular sheet which is to form end 31 of the diaper. The next step is to unfold the tubular sheet and refold it with a 90° reorientation, so that the folded edges form edges 22 and 24 of the pouch, these folded edges being in the preferred embodiment substantially equidistant from the slit 68. One method of accomplishing this is to slide the tubular sheet over a refolding mandrel which comprises two planar surfaces intersecting each other at approximately 90°; 71 is a schematic view of a segment of such a refolding mandrel, which is known in the art. Thus, the reformed edges which also coincide with the fold edges 22 and 24 will be formed along the edges 72 of the mandrel. The next step is to bring the slit and refolded sheet into position for attachment to the absorbent pad 12 so that the attachment can be made with the edges of the sheet and pad properly aligned.

It will be apparent that each individual diaper can be made in accordance with the previous steps on an intermittent basis. Preferably, however, the previous steps are accomplished in a continuous process which proceeds in a manner illustrated in FIG. 7. Specifically, the tubular sheet 60 is rolled off a roll 74 having a length considerably in excess of the length of an individual diaper, the slitting steps occurring periodically so as to space the slits along the tubular sheet 60 as it unwinds from the roll 74. After a portion of the tubular sheet is so slit, that portion passes over the mandrel so as to be refolded. From the mandrel, the sheet continues on to a station which is opposite a long roll 78 of the absorbent pad 12. The roll 78 unwinds at the same speed as the tubular sheet is traveling, and the sheet and the pad are brought into superposition and continuously adhered or otherwise attached to each other by an attaching station (not shown) using techniques such as heat sealing. Thereafter, individual diapers are periodically severed from the continuous length of adhered pad and sheet, the severing being spaced so as to intercept the slits which were formed along the line 68 at the point where it terminates at the top end 31 of the diaper. The final severing not only produces each individual diaper but completes the cut necessary to release the wings so that they can be unfolded from the layer 16 when the diaper is ready to be used. The bottom edge 26 of the layers 14 and 16 is sealed in a concurrent or subsequent operation. It will be recognized that this continuous process of making the improved disposable diaper reduces the cost by speeding up the process.

Although the invention has been described in connection with certain preferred embodiments, it is not intended that the invention be limited thereto. For example, the only requirement with respect to the slits in the pouch is that they assume a general T-configuration. Thus, the longitudinal slit can be positioned at any point along the width of the diaper, thus providing wings of unequal width. Also, the wings can be trimmed after manufacture to smaller dimensions. Furthermore, the two layers of fluid impervious sheet can be formed separately rather than as an integral sheet, the two layers then being heat sealed at their edges. Also, if desired, the pouch can open at both ends, allowing disposal to be accomplished by inverting the diaper inside out at either end of the pouch. While "slit" has been illustrated as a continuous severance, the term is meant to include such equivalents as a perforated tear line. Thus, it is intended that the invention cover all alternative arrangements, equivalents, and embodiments as may be included within the scope of the following claims.

What is claimed is:

1. A method of making the pouch for a disposable diaper having a fluid absorbent body and pouch integrate therewith, said fluid absorbent body having a front side and a back side, said back side having a fluid impervious surface and said pouch having a wall portion thereof common with said impervious surface in at least one waist region of the diaper and in at least a portion of the remaining region of the diaper, the remainder of the pouch wall comprising a supple, fluid impervious sheet attached to said body whereby said impervious surface and said sheet form opposing wall portions of said pouch, said method comprising slitting a flattened tube of fluid impervious sheet material a. through two opposing wall portions thereof along a line transverse to the longitudinal axis of the tube from a longitudinal edge of the flattened tube partially across the width of said flattened tube and b. along a line extending longitudinally from one end of the flattened tube to said transverse slit, with the longitudinal slit being closer said longitudinal edge than an inner portion of the transverse slit.

2. The method of claim 1 wherein said longitudinal slit extends along the longitudinal edge of the flattened tube.

3. The method of claim 1 wherein said transverse slit forms an angle of less than 90° with said longitudinal slit.

4. The method of claim 1 wherein said transverse slit extends one-half the width of said flattened tube.

* * * * *